(12) United States Patent
Joyce

(10) Patent No.: US 6,194,180 B1
(45) Date of Patent: *Feb. 27, 2001

(54) NUCLEIC ACID ENZYMES FOR CLEAVING DNA

(75) Inventor: Gerald F. Joyce, Encinitas, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/183,734

(22) Filed: Jan. 19, 1994

Related U.S. Application Data

(63) Continuation of application No. 08/007,732, filed on Jan. 22, 1993, now abandoned, which is a continuation of application No. 07/464,530, filed on Jan. 12, 1990, now abandoned.

(51) Int. Cl.[7] .............................. C07H 21/04; C12Q 1/68; C12N 15/85

(52) U.S. Cl. ............................ 435/91.31; 435/6; 435/325; 435/333; 536/23.1; 536/23.2; 536/24.5

(58) Field of Search .................................. 536/23.1, 23.2, 536/24.5; 435/6, 91.31, 325, 333

(56) References Cited

U.S. PATENT DOCUMENTS

| | | | |
|---|---|---|---|
| 4,987,071 | 1/1991 | Cech et al. | 435/71.31 |
| 5,180,818 | 1/1993 | Cech et al. | 536/23.1 |

OTHER PUBLICATIONS

Cech, *Science* 236: 1532–1539 (1987).
Burch, *Gene* 73: 273–294 (1988).
Sugimoto, et al., *Nucl. Acid Res.* 17: 355–371 (1989).
Joyce, et al., *Nucl. Acid Res.* 17: 7879–7889 (1989).
Doudna, et al., *Nature* 339: 519–522 (1989).

*Primary Examiner*—Robert A. Schwartzman
*Assistant Examiner*—Andrew Wang
(74) *Attorney, Agent, or Firm*—Thomas Fitting; Emily Holmes

(57) ABSTRACT

The present invention discloses nucleic acid enzymes capable of cleaving single-stranded DNA in a site specific manner.

5 Claims, 11 Drawing Sheets

ENDONUCLEASE

KINASE
LIGASE
PHOSPHATASE

NUCLEIC ACID ENZYMES FOR CLEAVING DNA

CROSS REFERENCE TO RELATED APPLICATIONS

The present application is a continuation of U.S. application Ser. No. 08/007,732, filed Jan. 22, 1993, now abandoned, which is a continuation of U.S. application Ser. No. 07/464,530, filed Jan. 12, 1990, now abandoned, the disclosures of which are incorporated by reference herein.

DESCRIPTION

This invention was made with government support under NASA Grant No. NAGW-1671. The government may have certain rights in the invention.

TECHNICAL FIELD

The present invention relates to nucleic acid enzymes for cleaving DNA.

BACKGROUND

Some genes have their coding sequences interrupted by stretches of non-coding DNA. These non-coding sequences are termed introns. To produce a mature transcript from these genes, the primary RNA transcript (precursor RNA) must undergo a cleavage-ligation reaction termed RNA splicing. This RNA splicing produces the mature transcript of the polypeptide coding messenger RNA (mRNA), ribosomal RNA, or transfer RNA (tRNA). Introns are grouped into four categories (Groups I, II, III, and IV) based on their structure and the type of splicing reaction they undergo.

Of particular interest to the present invention are the Group I introns. Group I introns undergo an intra-molecular RNA splicing reaction leading to cyclization that does not require protein cofactors, Cech, Science, 236:1532–1539 (1987).

The Group I introns, including the intron isolated from the large ribosomal RNA precursor of Tetrahymena thermophila, have been shown to catalyze a sequence-specific phosphoester transfer reaction involving RNA substrates. Zaug and Cech, Science, 229:1060–1064 (1985); and Kay and Inoue, Nature, 327:343–346 (1987). This sequence-specific phosphoester transfer reaction leads to the removal of the Group I intron from the precursor RNA and ligation of two exons in a process known as RNA splicing. Splicing reaction catalyzed by Group I introns proceeds via a two-step transesterification mechanism. The details of this reaction have been recently reviewed by Cech, Science, 236:1532–1539 (1987).

The splicing reaction of Group I introns is initiated by the binding of guanosine or a guanosine nucleotide to a site within the Group I intron structure. Attack at the 5' splice site by the 3'-hydroxyl group of guanosine results in the covalent linkage of guanosine to the 5' end of the intervening intron sequence. This reaction generates a new 3'-hydroxyl group on the uridine at the 3' terminus of the 5' exon. The 5' exon subsequently attacks the 3' splice site, yielding spliced exons and the full-length linear form of the Group I intron.

The linear Group I intron usually cyclizes following splicing. Cyclization occurs via a third transesterification reaction, involving attack of the 3'-terminal guanosine at an interval site near the 5' end of the intron. The Group I introns also undergo sequence specific hydrolysis reaction at the splice site sequences as described by Inoue et al., J. Mol. Biol., 189:143–165 (1986). This activity has been used to cleave RNA substrates in a sequence specific manner by Zaug et al., Nature, 324:429–433 (1986).

The structure of Group I introns has been recently reviewed by J. Burke, Gene, 73:273–294 (1988). The structure is characterized by nine base paired regions, termed P1–P9 as described in Burke et al., Nucleic Acids Res., 15:7217–7221 (1987). The folded structure of the intron is clearly important for the catalytic activity of the Group I introns as evidenced by the loss of catalytic activity under conditions where the intron is denatured. In addition, mutations that disrupt essential base-paired regions of the Group I introns result in a loss of catalytic activity. Burke, Gene, 73:273–294 (1988). Compensatory mutations or second-site mutations that restore base-pairing in these regions also restore catalytic activity. Williamson et al., J. Biol. Chem., 262:14672–14682 (1987); and Burke, Gene, 73:273–294 (1988).

Several different deletions that remove a large nucleotide segment from the Group I introns (FIG. 2) without destroying its ability to cleave RNA have been reported. Burke, Gene, 73:273–294 (1988). However, attempts to combine large deletions have resulted in both active and inactive introns. Joyce et al., Nucleic Acid Res., 17:7879 (1989).

To date, Group I introns have been shown to cleave substrates containing either RNA, or RNA and DNA. Zaug et al., Science, 231:470–475 (1986); Sugimoto et al., Nucleic Acids Res., 17:355–371 (1989); and Cech, Science, 236:1532–1539 (1987). A DNA containing 5 deoxycytosines was shown not to be a cleavage substrate for the Tetrahymena IVS, a Group I intron by Zaug et al., Science, 231:470–475 (1986).

BRIEF SUMMARY OF THE INVENTION

It has now been discovered that Group I introns have the ability to cleave single-stranded DNA substrates in a site specific manner.

Therefore the present invention provides a method of cleaving single-stranded DNA at the 3'-terminus of a predetermined nucleotide sequence present within single-stranded DNA. The single-stranded DNA is treated under DNA cleaving conditions with an effective amount of an endodeoxyribonuclease of the present invention where the DNA cleaving conditions include the presence of $MgCl_2$ at a concentration of at least 20 millimolar.

The present invention also contemplates a composition containing an endodeoxyribonuclease enzyme of the present invention, single-stranded DNA and magnesium ion at a concentration of greater than 20 millimolar.

The present invention further contemplates an endodeoxyribonuclease enzyme capable of cleaving single-stranded DNA at a predetermined nucleotide sequence where the enzyme has a nucleotide sequence defining a recognition site that is contiguous or adjacent to the 5'-terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3'-terminal to the second stem loop, and a third stem loop located 3'-terminal to the third spacer region, the third stem loop comprising a 5' stem portion interrupted by a nucleotide sequence defining a P3[3'] region capable of hybridizing to the P3[5'] region.

BRIEF DESCRIPTION OF THE DRAWINGS

In the drawings forming a portion of this disclosure:

In FIGS. 2A–2C, the secondary structure of the *T. thermophila* pre-rRNA intron, with the recognition sequence and the core structure that is the most conserved region among group I introns shown in bold. The nomenclature used to denote various structural features is the standard nomenclature described in Burke et al., *Nucleic Acids Pes.* 15:7217–7221 (1987). The nine conserved pairing regions, P1–P9, and the various loops are shown. The nucleotide sequence is numbered beginning at the 5' terminus of the molecule.

Figure 1A:
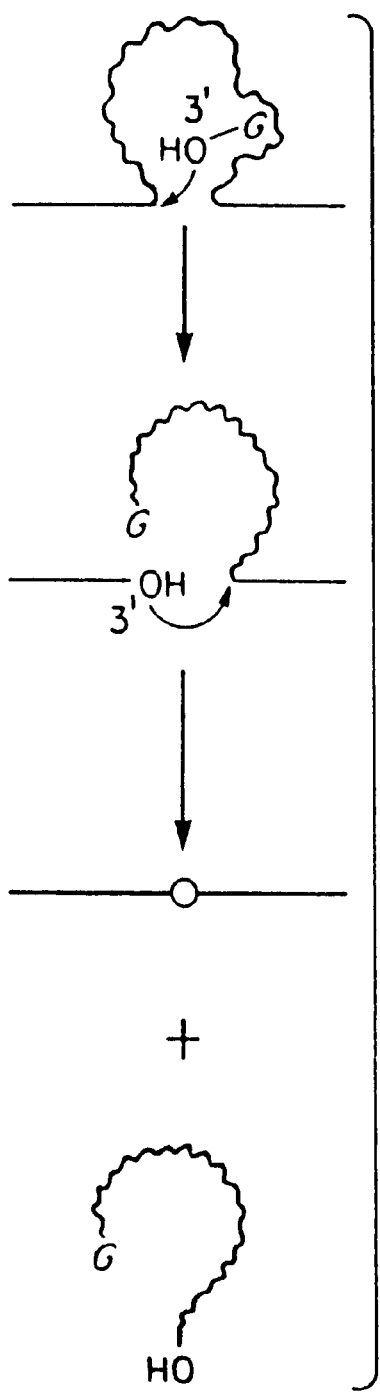
In FIGS. 1A–1D, the splicing mechanisms of the four major groups of precursor RNAs. Wavy lines indicate introns, smooth lines indicate flanking exons. For nuclear mRNA splicing, many components assemble with the pre-mRNA to form the spliceosome; only two, the U1 and U2 small nuclear ribonucleoproteins, are shown. Nuclear tRNA splicing is described by Greer et al., TIBS 9:139–41(1984).
Figure 1B:
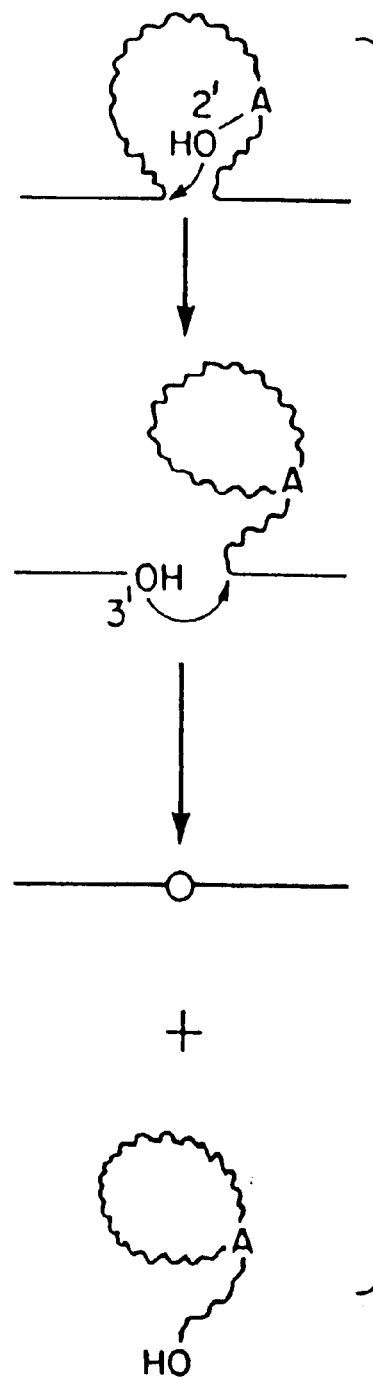
Figure 1C:
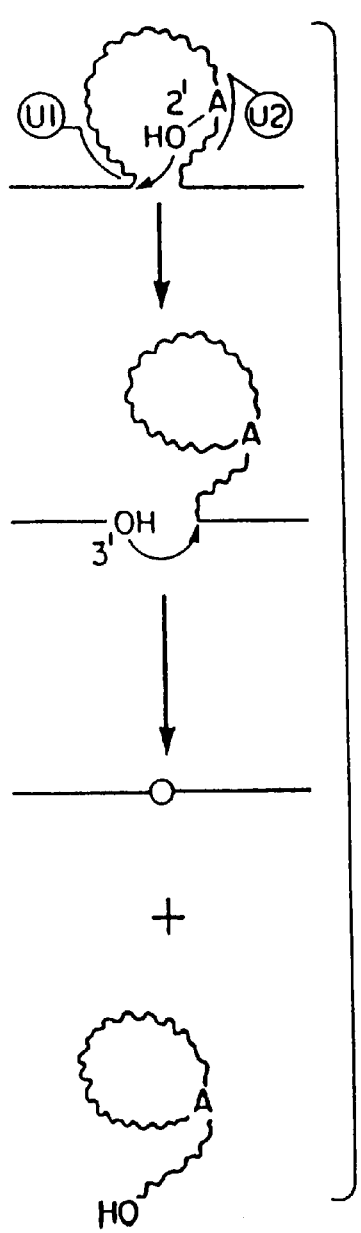
Figure 1D:
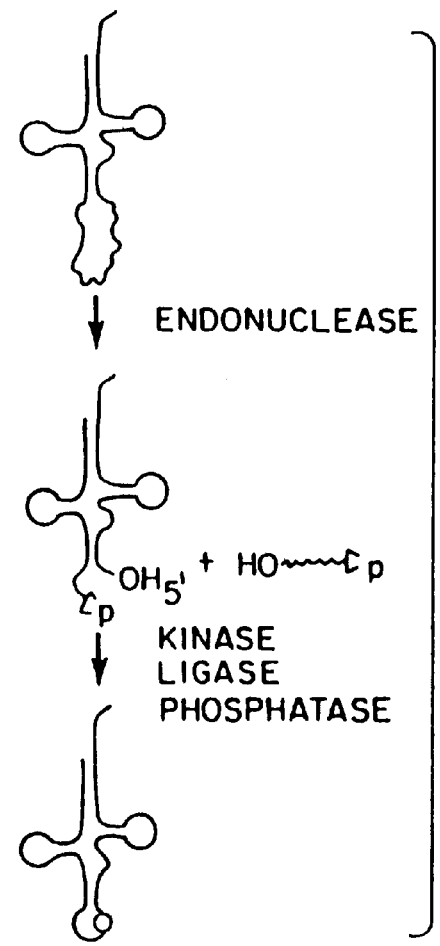

The recognition site is located at nucleotide 19 to 27, the first spacer region is located at nucleotides 27 to 28 and 94 to 95, the P3[5'] region is located at nucleotides 96 to 103, the second spacer region is located at nucleotides 104 to 106, the first stem loop is located at nucleotides 107 to 214, the second stem loop is located at nucleotides 215 to 258, the third spacer region is located at nucleotides 259 to 261 and the third stem loop is located at nucleotides 262 to 314.

Figure 3A:
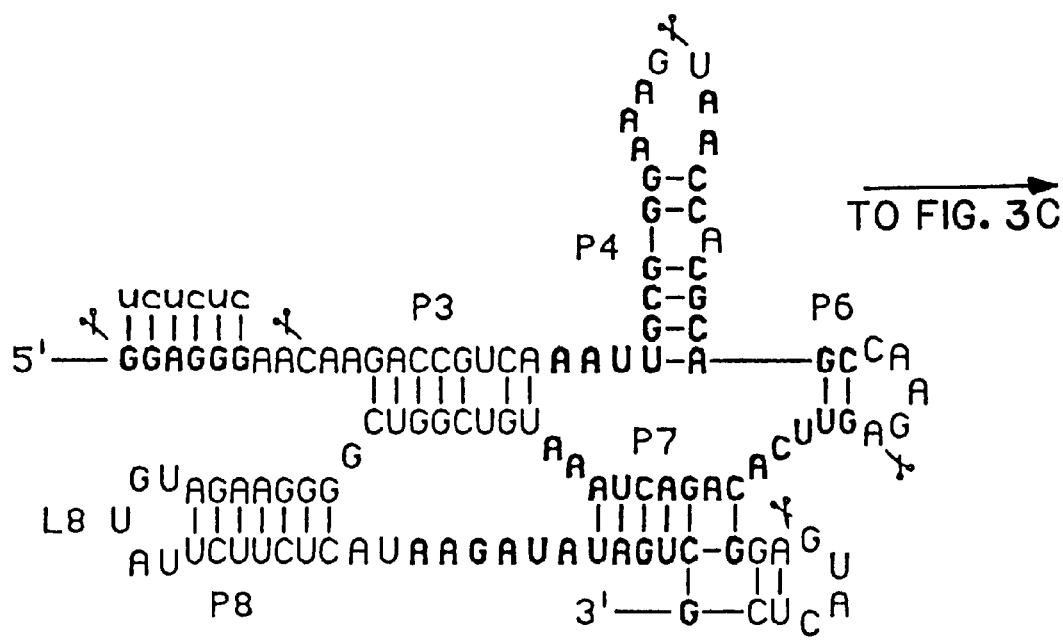
Figure 3B:
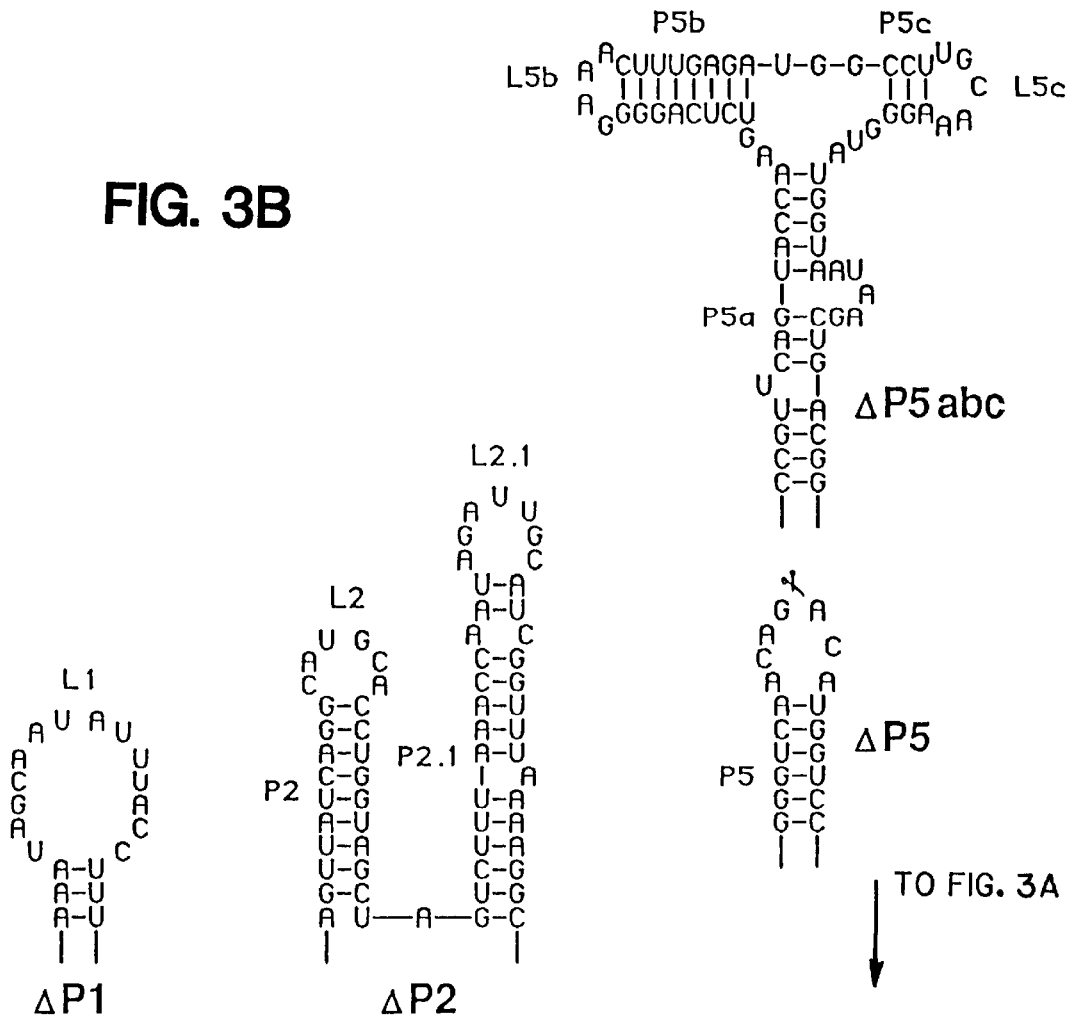
Figure 3C:
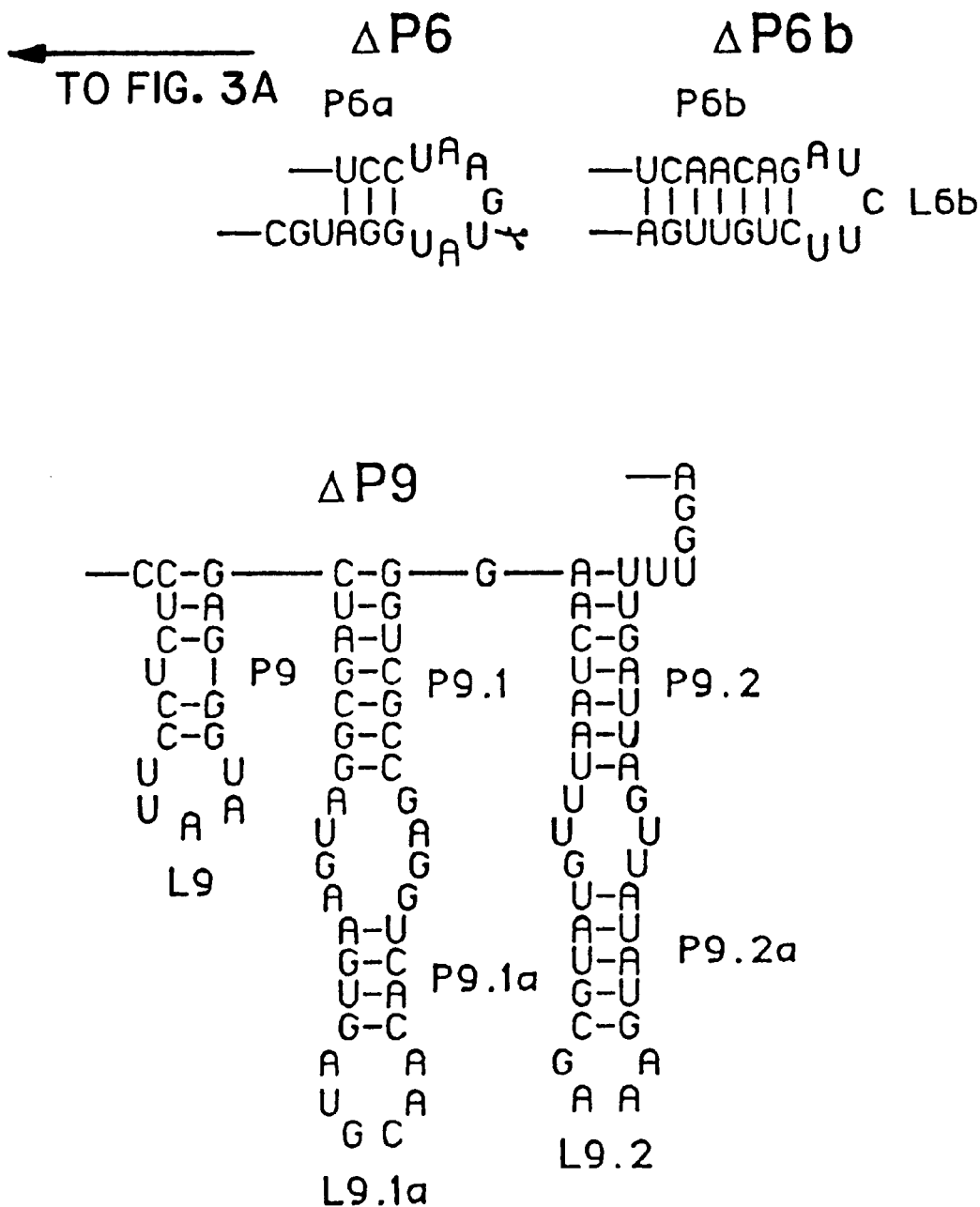

In FIGS. 3A–3C, the various deletions removing portions of the *T. thermophili* pre-rRNA intron are shown. The nomenclature used is the same nomenclature defined in Burke et al., *Nucleic Acids Research,* 15:7217–7221 (1987). The nucleotide segments removed in each deletion are shown with the greek character delta followed by the number of the pairing region removed. Combination of deletions are noted as Delta P 2/9 for example.

Figure 4:
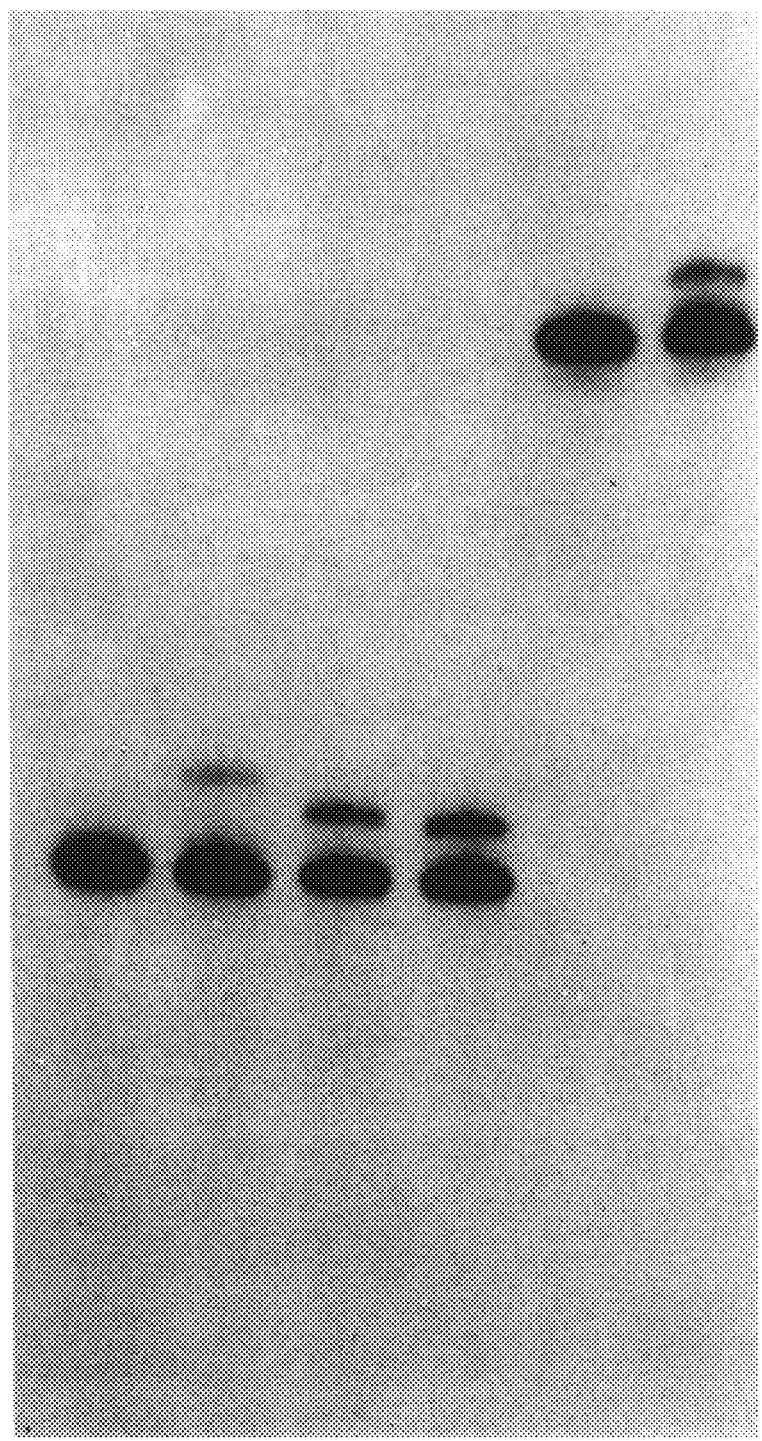

In FIG. 4, trans-splicing activity of the wild-type and ΔP9 mutant form of the Tetrahymena ribozyme using the substrate GGCCCUCU.A$_3$UA$_3$UA$_3$(S1), d(GGCCCTCU.A$_3$TA$_3$TA) (S2), or d(GGCCCTCT.A$_3$TA$_3$TA) (S3) are shown.

Figure 5:
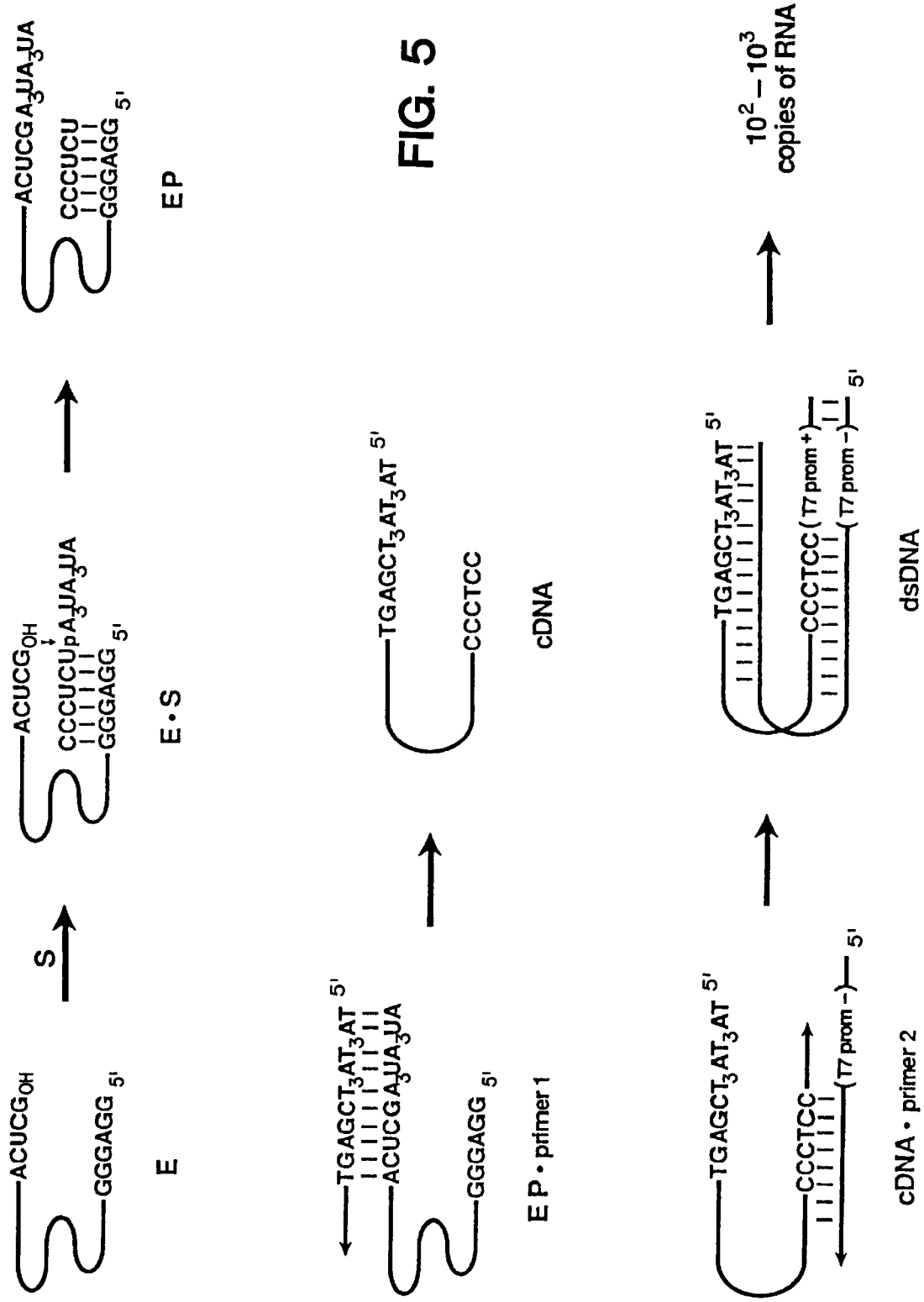

In FIG. 5, selective amplification of the Tetrahymena ribozyme (E) based on its ability to react with an oligonucleotide substrate (S) is shown. Top, the L-21 form of the ribozyme binds an oligopyrimidine-containing RNA substrate by complementary pairing. The 3'-terminal G$_{OH}$ of the ribozyme attacks the phosphodiester bond following a sequence of pyrimidines, resulting in transfer of the 3' portion of the substrate to the 3' end of the ribozyme. Middle, the product of the RNA-catalyzed reaction offers a unique site for hybridization of an oligodeoxynucleotide used to initiate cDNA synthesis. Bottom, a primer containing the T7 promoter is hybridized to the cDNA, the second strand of the promoter is completed, the DNA is transcribed to RNA.

Figure 6:
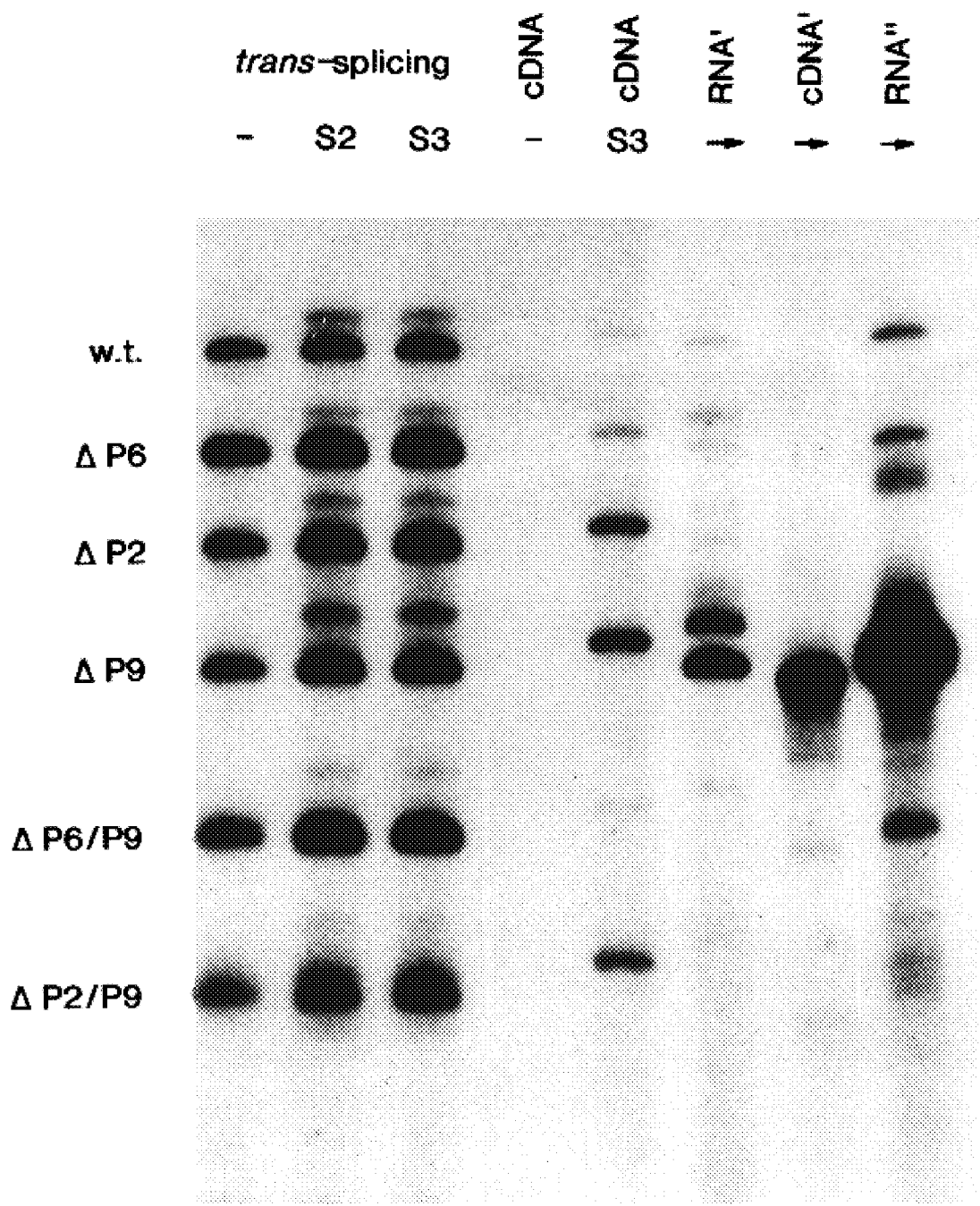

In FIG. 6, selective amplification of an ensemble of structural variants of the Tetrahymena ribozyme based on their ability to carry out a trans-splicing reaction with a DNA substrate. Lanes 1–3, trans-splicing with no substrate, the RNA substrate GGCCCUCU.A$_3$UA$_3$UA, and the DNA substrate d(GGCCCTCT.A$_3$TA$_3$TA). Lanes 4–5, selective cDNA synthesis of trans-spliced products. Lanes 6–8, successive rounds of transcription and reverse transcription leading to amplification of selected materials. Materials were separated by electrophoresis in a 5% polyacrylamide/8M urea gel, an autoradiogram of which is shown.

DETAILED DESCRIPTION OF THE INVENTION

A. Enzymes

An endodeoxyribonuclease of the present invention is capable of cleaving a single-stranded DNA substrate. Typically, the endodeoxyribonuclease is also capable of cleaving a single-stranded RNA substrate or a modified DNA substrate containing a uracil at the cleavage site rather than a thymine.

The term ribozyme is used to describe an RNA containing nucleic acid that is capable of functioning as an enzyme. Ribozymes include endoribonucleases and endodeoxyribonucleases of the present invention.

An endodeoxyribonuclease of the present invention may be RNA, modified RNA, RNA-DNA polymer, a modified RNA-DNA polymer, a modified DNA-RNA polymer or a modified RNA-modified DNA polymer. RNA contains nucleotides containing a ribose sugar and adenine, guanine, uracil or cytosine as the base at the 1' position. Modified RNA contains nucleotides containing a ribose sugar and adenine, thymine, guanine or cytosine and optionally uracil as the base. A RNA-DNA polymer contains nucleotides containing a ribose sugar and nucleotides containing deoxyribose sugar and adenine, thymine and/or uracil, guanine or cytosine as the base attached to the 1' carbon of the sugar. A modified RNA-DNA polymer is comprised of modified RNA, DNA and optionally RNA. Modified DNA contains nucleotides containing a deoxyribose sugar and nucleotides containing adenine, uracil, guanine, cytosine and possibly thymine as the base. A modified DNA-RNA polymer contains modified DNA, RNA and optionally DNA. A modified RNA-modified DNA polymer contains modified RNA-modified DNA, and optionally RNA and DNA.

An endodeoxyribonuclease of the present invention is capable of cleaving DNA 3' of a predetermined base sequence. In addition, an endodeoxyribonuclease of this invention is characterized by a nucleotide sequence defining a recognition site that is contiguous or adjacent to the 5' terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3-'terminal to the second stem loop, and a third stem loop located 3'-terminal to the third spacer region, the third stem loop comprising a 5' stem portion defining a P3[3'] region capable of hybridizing to the P3[5'] region.

The recognition site of an endodeoxyribonuclease of the present invention contains a sequence of at least 2 to about 8 bases preferably about 4 to about 7 bases, capable of hybridizing to a complementary sequence of bases within the substrate nucleic acid giving the endodeoxyribonuclease its high sequence specificity. For example, an endodeoxyribonuclease of the present invention with a recognition site base sequence of 5'-GGAGG-3' is able to recognize the base sequence 5'-CCCTCT-3' present within the single-stranded DNA substrate (see Example 2). This same recognition site also allows the endodeoxyribonuclease to cleave modified DNA substrates with high sequence specificity (see Example 2.)

The exact bases present in the recognition site determine the base sequence at which cleavage will take place. Cleavage of the substrate nucleic acid occurs immediately 3' of the substrate cleavage sequence, the substrate nucleotide sequence that hybridizes to the recognition site. This cleavage leaves a 3' hydroxyl group on the substrate cleavage sequence and a 5' phosphate on the nucleotide that was originally immediately 3' of the substrate cleavage sequence in the original substrate. Cleavage can be redirected to a site of choice by changing the bases present in the recognition sequence (internal guide sequence). See Murphy et al., *Proc. Natl. Acad. Sci., USA,* 86:9218–9222 (1989). (The disclosures of all references cited within this document are incorporated by reference.) In addition, any combination of bases may be present in the recognition site if a polyamine is present. See, for example, Doudna et al., *Nature,* 339:519–522 (1989). Typically, the polyamine is either spermidine, putrescine or spermine. A spermidine concentration of about 5 mM was shown to be effective. The recognition site may also be provided as a separate nucleic acid, an external recognition site not covalently coupled to the rest of the endodeoxynuclease. External recognition sites have been shown to direct endoribonuclease cleavage at a specific base sequence by Doudna et al., *Nature,* 339:519–522 (1989). If an external recognition site is used, the endodeoxyribonuclease used with it would not contain a recognition site but would comprise a P3[5'] region, a second spacer region, a first stem loop, a second stem loop, a third spacer region and a third stem loop where the third stem loop comprises a 5' stem portion defining a P3[3'] region capable of hybridizing to said P3[5'] region.

Use of an endodeoxyribonuclease of the present invention with an external recognition site would allows the target sequence to be changed by merely changing the external recognition site sequence. Use of a plurality of different external recognition sequences with an endodeoxyribonuclease of the present invention allows the substrate nucleic acid to be cleaved at each of the different base sequences encoded by the external recognition sequences.

First spacer regions typically contain a sequence of nucleotides about 3 bases to about 7 bases, preferably about 5, bases in length. Preferably, the nucleotides making up the first spacer have the sequence 5'-NNNNA-3', where N represents the presence of any nucleotide at that position. More preferably, the first spacer region is defined by the sequence 5'-AACAA-3'.

In other preferred embodiments, the first spacer region is comprised of a nucleotide sequence defining two spacer stem loops. Preferably, the first spacer stem loop is 25 nucleotides in length, and the second spacer stem loop is 36 bases in length. More preferably, the first spacer stem loop has the base sequence, 5'-AGUUACCAGGCAUGCACCUGGUAGUCA-3', and the second spacer stem loop has the base sequence, 5'-GUCUUUAAACCAAUAGAUU-GGAUCGGUUUAAAAGGC-3'.

A stem loop is a secondary structure formed by a nucleotide sequence that has "folded over on itself". A stem loop comprises a 5' nucleotide sequence portion, designated a 5' paring segment (P[5']) that is capable of hybridizing to a nucleotide sequence located 3' of the P[5'] and is designated the 3' pairing segment (P[3']). In a stem loop, the P[5'] and P[3'] are connected by a nucleotide sequence called a loop. The P[5'] and P[3'] hybridize and form a nucleic acid duplex. The nucleic acid duplex formed by the P[5'] and P[3'] does not have to be a perfect duplex and may contain stretches of nucleotides that are either unpaired or paired to a sequence outside the stem loop.

In preferred embodiments, the P3[5'] region is an eight nucleotide sequence. The eight nucleotides present in the P3[5'] region may be any eight nucleotides as long as the P3[5'] region is capable of hybridizing with the P3[3'] region to form the third pairing segment or P3 shown in FIG. 2. The formation of P3 by P3[5'] region and P3[3'] region are required for catalytic activity as has been recently reviewed by John Burke, *Gene,* 73:273–294 (1988).

More preferably, the P3[5'] has the nucleotide sequence, 5'-GACCGUCA-3'. However, changes in the P3[5'] region nucleotide sequences may be made as long as P3 is still able to form or if compensating changes in the P3[3'] region nucleotide sequence have been made as has been demonstrated by Williamson et al., *J. Biol. Chem.,* 262:14672–14682 (1987).

In preferred embodiments, the second spacer region is about three nucleotides in length. Typically, any three nucleotides may make up the second space region as long as the ribozyme containing this spacer has the desired catalytic activity.

More preferably, the second spacer region has the nucleotide sequence, 5'-AAU-3'. However, this sequence may be changed as long as the desired catalytic activity is retained.

In preferred embodiments, the first stem loop is about 108 nucleotides in length. More preferred, the first stem loop corresponds to nucleotides 107 to 214 of FIG. 2. The ten most 5'-terminal nucleotides (nucleotides 107 to 117 of FIG. 2) and the ten most 3'-terminal nucleotides (nucleotides 204 to 214 of FIG. 2) of the first stem loop are the most critical for known catalytic functions. See, for example, John Burke, *Gene,* 73:273–294 (1988).

In other preferred embodiments, the first stem loop is about 39 nucleotides in length. More preferred, the first stem loop corresponds to nucleotides 107 to 126 and nucleotides 196 to 214 in FIG. 2, where nucleotide 126 is directly linked to nucleotide 196.

In another preferred embodiment, the first stem loop is 20 nucleotides in length. More preferred, the first stem loop corresponds to nucleotides 107 to 116, and nucleotides 205 to 214 of FIG. 2, where nucleotide 116 is directly linked to nucleotide 205.

In preferred embodiments, the second stem loop is about 44 nucleotides in length. More preferred, the first stem loop corresponds to nucleotides 215 to 258 in FIG. 2. The 5 most 5'-terminal nucleotides (nucleotides 215 to 219 in FIG. 2) and the 5 most 3'-terminal nucleotides (nucleotides 254 to 258 in FIG. 2) of the second stem loop are the most critical for known catalytic functions. See for example, John Burke, *Gene,* 73: 273–294 (1988).

In other preferred embodiments, the second stem loop is about 25 nucleotides in length. More preferably, the second stem loop nucleotide sequence substantially corresponds to nucleotides 215 to 227 and nucleotides 247 to 258 in FIG. 2, where nucleotides 227 and 247 are directly linked. In another preferred embodiment, the second stem loop is about 9 nucleotides in length. More preferably, the second stem loop substantially corresponds to nucleotides 215 to 220 and 256 to 258 in FIG. 2 where nucleotides 220 and 256 are directly linked.

In preferred embodiments, the third spacer region is about 3 nucleotides in length. More preferably, the third spacer region corresponds to nucleotides 259 to 261 of FIG. 2. Some nucleotide changes can be made in the third spacer region while still preserving the desired catalytic activity. See for example, Williamson et al., *J. Biol. Chem.,* 262:14672–14682 (1987), where the nucleotide at position 259 was changed to A and the nucleotide at 261 was changed to a C while maintaining splicing activity. The nucleotide at position 260 (FIG. 2) was changed to either G, A or U while preserving the desired catalytic activity as reported in John Burke, *Gene,* 73:273–294 (1988).

In preferred embodiments, the third stem loop is about 51 nucleotides in length. These 51 nucleotides are divided into a 5' stem portion defining a P3[3'] region that is capable of hybridizing to the P3[5'] region, a loop and a 3' stem portion. Preferably, the P3[3'] region is about 8 nucleotides in length. However, the length of the P3[3'] may vary to correspond with the length of the P3[5'] region. Preferably, the P3[3'] region begins about 10 nucleotides from the 5' end of the third stem loop.

Figure 2A:
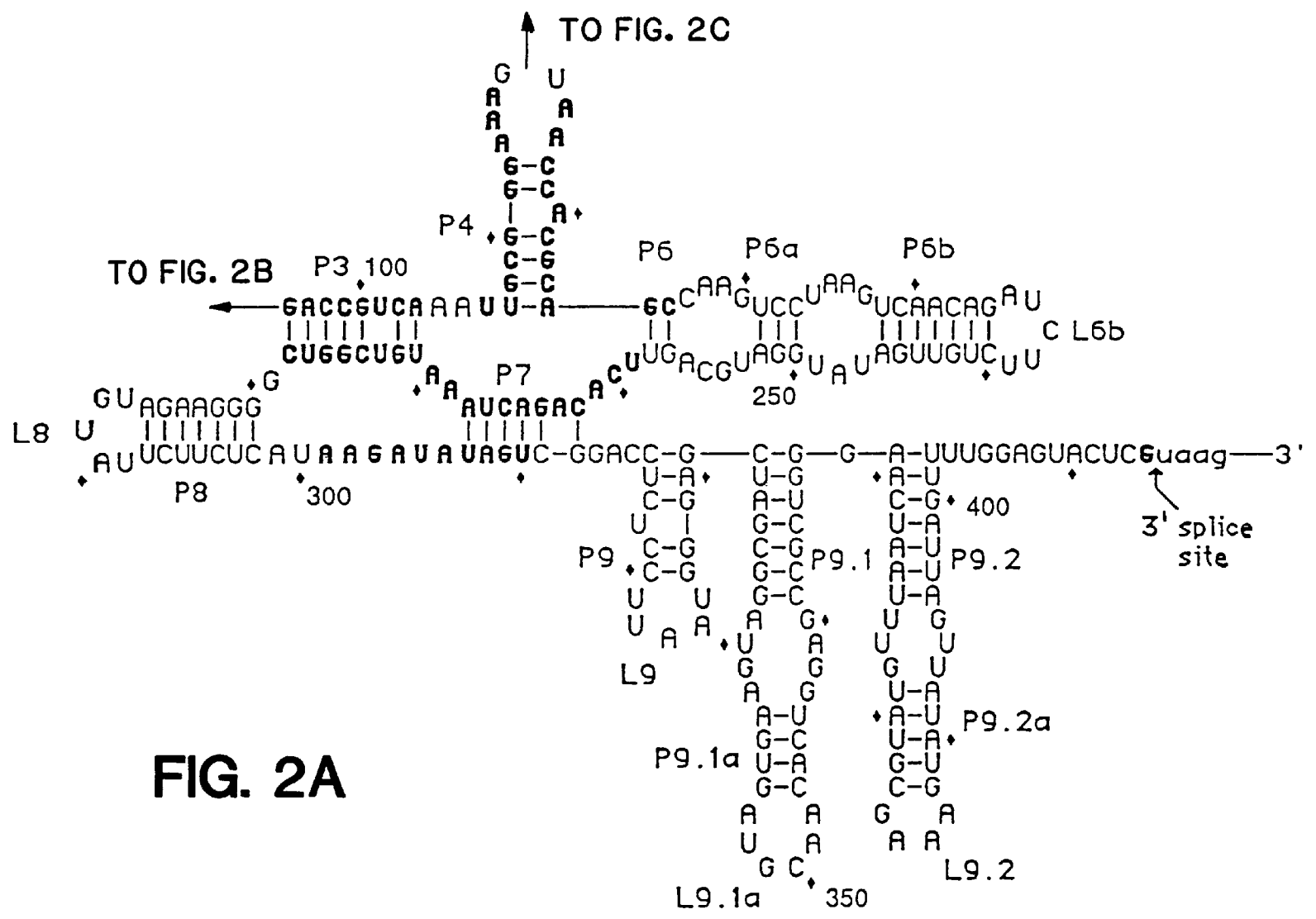
Figure 2B:
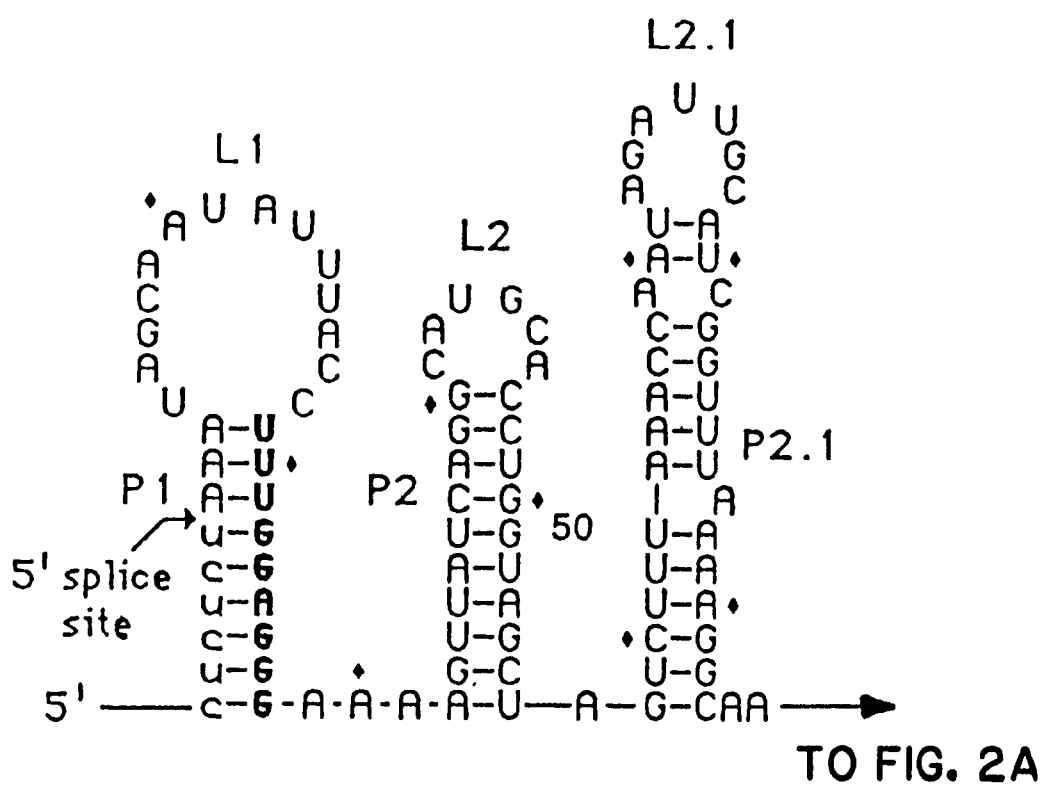
Figure 2C:
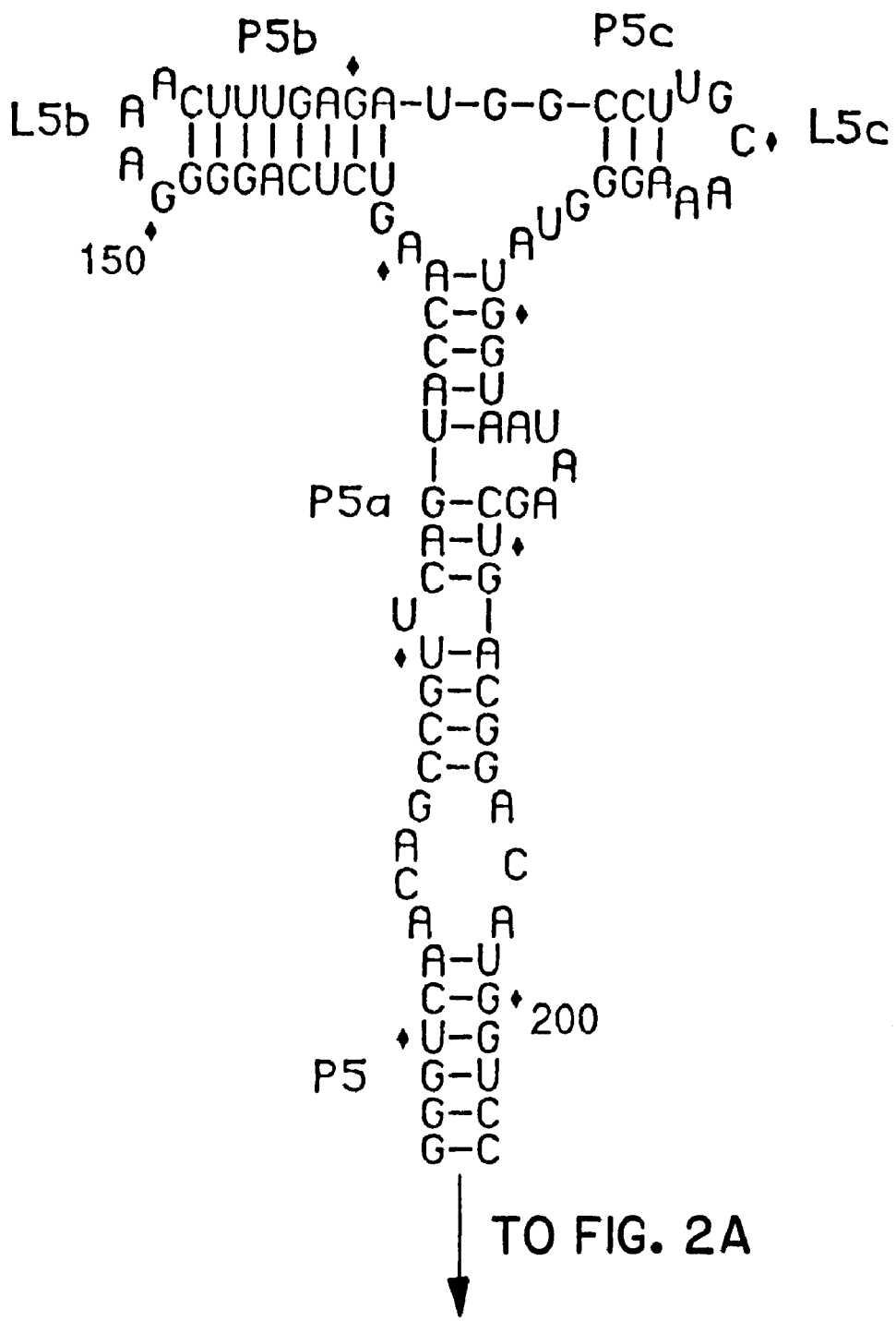

More preferably, the third stem loop is 5 nucleotides in length and those nucleotides substantially correspond to nucleotides 262 to 312 in FIG. 2. Preferably, the P3[3'] region is about 8 nucleotides in length and those nucleotides substantially correspond to nucleotides 271 to 278 in FIG. 2. Changes, including deletions, mutations, reversions and insertions, can be made within the third stem loop and the P3[3'] region and still maintain the desired catalytic activity. See, for example, Burke et al., *Cell,* 45:167–176 (1986) and Williamson et al., *J. Biol. Chem.,* 262:14672–14682 (1987), where nucleotide 266 was changed to G and a compensatory mutation changing nucleotide 309 to C was made while maintaining the desired catalytic activity. Other mutations, including changing nucleotide 268 to C and at the same time changing nucleotide 307 to C, and changing nucleotide 268 to U and at the same time changing nucleotide 307 to A, were also shown to maintain the desired catalytic activity.

Other changes in the nucleotide sequence of the third stem loop are also contemplated by the present invention. Changing nucleotides 301 to C (FIG. 2), 302 to 6, and 303 to C has been shown to eliminate transesterification activity, but does not eliminate site specific cleavage or GTP binding by Williamson et al., *J. Biol. Chem.,* 262:14672–14682 (1987).

Changes in nucleotides 280 and 282 (FIG. 2) together with compensatory changes in nucleotides 296 and 298 have been shown to preserve the desired catalytic function as reported in J. Burke, *Gene,* 73:273–294 (1988). Mutations such as these preserve a given secondary structure and these and similar mutations would be expected to maintain the desired catalytic activity.

Changes in the P3[3'] region, nucleotides 272 and 274 (FIG. 2), along with compensatory changes in nucleotides 100 and 102, were made while maintaining the desired catalytic activity by Williamson et al., J. Biol. Chem., 262:14672–14682 (1987) and Inoue et al., Cell, 43:431–437 (1985). Changes similar to those changes made above will maintain the desired catalytic activity as long as the particular secondary structure such as a stem loop, pairing region or spacer is maintained.

An endodeoxyribonuclease of the present invention may also include additional stem loops located 3'-terminal to the third stem loop. These additional stem loops may contain any number of stem loops as long as the desired catalytic activity is maintained. Preferably, any additional stem loops have a nucleotide sequence that substantially corresponds to nucleotides 316 to 402 of FIG. 2.

In preferred embodiments, an endodeoxyribonuclease of the present invention may combine one or more of the mutations described above. Typically, these deletions change the length of or alter the nucleotide sequence of a stem loop, the P3[5'], the P3[3'] region, a spacer region or the recognition sequence. The mutation within one catalytically active endodeoxyribonuclease may be combined with the mutation within a second catalytically active endodeoxyribonuclease to produce a new endodeoxyribonuclease containing both mutations.

In other preferred embodiments, an endodeoxyribonuclease of the present invention may have random or defined mutations introduced into it using a variety of methods well known to those skilled in the art. For example, the method described by Joyce et al., Nucleic Acids Research, 17:711–712 (1989), involves excision of template (coding) strand of double-stranded DNA, reconstruction of the template strand with inclusion of mutagenic oligonucleotides, and subsequent transcription of the partially-mismatched template. This allows the introduction of defined or random mutations at any position in the molecule by including polynucleotides containing known or random nucleotide sequences at selected positions. Alternatively, mutations may be introduced into the endodeoxyribonuclease by substituting 5-Br dUTP for TTP in the reverse transcription reaction. 5-Br dU can pair with dG in the "wobble" position as well as dA in the standard Watson-Crick position, leading to A to G and G to A transitions. Similarly, substituting 5-Br UTP for UTP in the forward transcription reaction would lead to C to U and U to C transitions in the subsequent found of RNA synthesis.

B. Methods

The method of the present invention is useful for cleaving any single-stranded nucleic acid including single-stranded DNA, modified DNA, RNA and modified RNA. The single-stranded nucleic acid must only be single-stranded at or near the substrate cleavage sequence so that an enzyme of the present invention can hybridize to the substrate cleavage sequence by virtue of its recognition sequence.

A single-stranded nucleic acid that will be cleaved by a method of this invention may be chemically synthesized, enzymatically produced or isolated from various sources such as phages, viruses or cells, including plant cells, eukaryotic cells, yeast cells and bacterial cells. Chemically synthesized single-stranded nucleic acids are commercially available from many sources including, Research Genetics, Huntsville, Ala. Single-stranded phages such as the M13 cloning vectors described by Messing et al., *Proc. Natl. Acad. Sci., USA,* 74:3642–3646 (1977), and Yanisch-Perron et al., *Gene,* 33:103–119 (1985). Bacterial cells containing single-stranded phages would also be a ready source of suitable single-stranded DNA. Viruses that are either single-stranded DNA viruses such as the parvoviruses or are partially single-stranded DNA viruses such as the hepatitis virus would provide single-stranded DNA that could be cleaved by a method of the present invention. Single-stranded RNA cleavable by a method of the present invention could be provided by any of the RNA viruses such as the picornaviruses, togaviruses, orthomyxoviruses, paramyxoviruses, rhabdoviruses, coronaviruses, arenaviruses or retroviruses.

The methods of this invention may be used on single-stranded nucleic acid that are present inside a cell, including eucaryotic, procaryotic, plant, mammalian, yeast or bacterial cell. Under these conditions a method of the present invention could act as an anti-viral agent or a regulatory of gene expression.

The method of the present invention cleaves single-stranded DNA at the 3'-terminus of a predetermined base sequence. This predetermined base sequence or substrate cleavage sequence may contain from 2 to 8 nucleotides. The method allows cleavage at any nucleotide sequence by altering the nucleotide sequence of the recognition site of the endodeoxyribonuclease. This allows cleavage of single-stranded DNA in the absence of a restriction endonuclease site at that position.

Cleavage at the 3'-terminus of a predetermined base sequence produces a single-stranded DNA, containing the substrate cleavage sequence, with a 3'-terminal hydroxyl group. In addition, the cleavage joins the remainder of the original single-stranded DNA substrate with the endodeoxyribonuclease enzyme. This cleavage reaction and products produced from this cleavage reaction are analogous to the cleavage reaction and cleavage products produced by the Tetrahymena ribozyme described by Zaug and Cech, Science, 231:470–475 (1986) and reviewed by T. R. Cech, Annual Rev. of Biochem., 59:(1990). The endodeoxyribonuclease of the present invention may be separated from the remainder of single-stranded DNA substrate by site-specific hydrolysis at the phosphodiester bond following the 3'-terminal guanosine of the endodeoxyribonuclease similar to the site-specific cleavage at this position described for the ribozyme acting on RNA by Inoue et al., J. Mol. Biol., 189:143–165 (1986). Separation of the endodeoxyribonuclease from the substrate allows the endodeoxyribonuclease to carry out another cleavage reaction.

Single-stranded DNA is treated under DNA cleaving conditions with an effective amount of an endodeoxyribonuclease of the present invention, where the DNA cleaving conditions include the presence of $MgCl_2$ at a concentration of at least 20 millimolar.

An effective amount of an endodeoxyribonuclease is the amount endodeoxyribonuclease required to cleave a predetermined base sequence present within the single-stranded DNA. Preferably, the endodeoxyribonuclease is present at a molar ratio of endodeoxyribonuclease to substrate cleavage sites of 1 to 20. This ratio may vary depending on the length of treating and efficiency of the particular endodeoxyribonuclease under the particular DNA cleavage conditions employed.

Treating typically involves admixing, in aqueous solution, the single-stranded DNA, the enzyme and the $MgCl_2$ to form a DNA cleavage admixture, and then maintaining the admixture thus formed under DNA cleaving conditions for a time period sufficient for the endodeoxyribonuclease to cleave the single-stranded DNA at any of the predetermined nucleotide sequences present in the single-stranded DNA.

Preferably, the amount of time necessary for the endodeoxyribonuclease to cleave the single-stranded DNA has been predetermined. The amount of time is from about 5 minutes to about 24 hours and will vary depending upon the concentration of the reactants, and the temperature of the reaction. Usually, this time period is from about 30 minutes to about 4 hours such that the endodeoxyribonuclease cleaves the single-stranded DNA at any of the predetermined nucleotide sequences present.

Preferably, the DNA cleaving conditions include the presence of $MgCl_2$ at a concentration of at least 20 mM. Typically, the DNA cleaving conditions include $MgCl_2$ at a concentration of about 20 mM to about 150 mM. The optimal $MgCl_2$ concentration to include in the DNA cleaving conditions can be easily determined by determining the amount of single-stranded DNA cleaved at a given $MgCl_2$ concentration. One skilled in the art will understand that the optimal $MgCl_2$ concentration may vary depending on the particular endodeoxyribonuclease employed.

Preferably, the DNA cleaving conditions are at from about pH 6.0 to about pH 9.0. One skilled in the art will understand that the method of the present invention will work over a wide pH range so long as the pH used for DNA cleaving is such that the endodeoxyribonuclease is able to remain in an active conformation. An endodeoxyribonuclease in an active conformation is easily detected by its ability to cleave single-stranded DNA at a predetermined nucleotide sequence. More preferably, the DNA cleaving conditions are at from about pH 7.0 to about pH 8.0. Most preferred are DNA cleaving conditions at about pH 7.5.

Preferably, the DNA cleaving conditions are at from about 15° C. to about 60° C. More preferably, the DNA cleaving conditions are from about 300° C. to about 56° C. The temperature of the DNA cleaving conditions are constrained only by the desired cleavage rate and the stability of that particular endodeoxyribonuclease at that particular temperature. Most preferred are DNA cleavage conditions from about 37° C. to about 50° C.

In other preferred methods the present invention contemplates DNA cleaving conditions including the presence of a polyamine. Polyamines useful practicing the present invention include spermidine, putrescine, spermine and the like. Preferably, the polyamine is spermidine and it is present at a concentration of about 1 mM to about 15 mM. More preferably, spermidine is present at a concentration of about 1 mM to about 10 mM. Most preferred, are DNA cleavage conditions including the presence of spermidine at a concentration of about 2 mM to about 5 mM.

The present invention also contemplates a method of producing a nucleic acid having a predetermined activity. Preferably, the desired activity is a catalytic activity.

A population of Group I nucleic acids is subjected to mutagenizing conditions to produce a diverse population of mutant nucleic acids.

In preferred embodiments, the population of Group I nucleic acids is made up of at least 2 Group I nucleic acids. Group I nucleic acids are nucleic acid molecules having at least a nucleic acid sequence defining a recognition site that is contiguous or adjacent to the 5'-terminus of the nucleotide sequence, a first spacer region located 3'-terminal to the recognition site, a P3[5'] region located 3'-terminal to the first spacer region, a second spacer region located 3'-terminal to the P3[5'] region, a first stem loop located 3'-terminal to the second spacer region, a second stem loop located 3'-terminal to the first stem loop, a third spacer region located 3'-terminal to the second stem loop, and a third stem loop located 3'-terminal to the third spacer region, the third stem loop comprising a 5' stem portion defining a P3[3'] region capable of hybridizing to the P3[5'] region.

In preferred embodiments, mutagenizing conditions include conditions that introduce either defined or random nucleotide substitutions within the Group I nucleic acid. Examples of typical mutagenizing conditions include conditions disclosed in other parts of this specification and the methods described by Joyce et al., NAR 17:711–722(1989) and Joyce, Gene, 82:83–87(1989).

In preferred embodiments, a diverse population of mutant nucleic acid contains at least 2 nucleic acid molecules that do not have the exact same nucleotide sequence.

A nucleic acid having a predetermined activity is selected from the diverse population of mutant nucleic acids on the basis of its ability to perform the predetermined activity.

In preferred embodiments, selecting includes any means of physically separating the mutant nucleic acids having a predetermined activity from the diverse population of mutant nucleic acids. Typically, selecting includes separation by size, the presence of a catalytic activity and hybridizing the mutant nucleic acid to another nucleic acid that is either in solution or attached to a solid matrix. Preferably, the predetermined activity is such that the mutant nucleic activity having the predetermined activity becomes labelled in some fashion by virtue of the activity. For example, the predetermined activity may be an endodeoxyribonuclease activity whereby the activity of the mutant nucleic acid upon its substrate causes the mutant nucleic acid to become covalently linked to it. The mutant nucleic acid is then selected by virtue of the covalent linkage.

In other preferred embodiment, selecting a mutant nucleic acid having a predetermined activity includes amplification of the mutant nucleic acid as described in Joyce, *Gene,* 82:83–87(1989).

D. Compositions

Also contemplated by the present invention are compositions containing an endodeoxyribonuclease enzyme of the present invention, single-stranded DNA and magnesium ion at a concentration of greater than 20 millimolar.

Preferably, the endodeoxyribonuclease is present at a concentration of about 0.05 µM to about 2 mM. Typically, the endodeoxyribonuclease is present at concentration ration of endodeoxyribonuclease to single-stranded DNA from about 1 to 5 to about 1 to 50. More preferably, the endodeoxyribonuclease is present in the composition at a concentration of about 0.1 µM to about 1 µM. Most preferred, are compositions containing the endodeoxyribonuclease at a concentration of about 0.1 µM to about 0.5 µM.

Preferably, single-stranded DNA is present in the composition at a concentration of about 0.5 µM to about 1000 µM. One skilled in the art will understand that there are many sources of single-stranded DNA including synthetic DNA, phage DNA, denatured double-stranded DNA, viral DNA and cellular.

Preferably, magnesium ion is present in the composition at a concentration of about 20 mM to about 200 mM. More preferably, the magnesium ion is present in the composition at a concentration of about 20 mM to about 150 mM. One skilled in the art will understand that the magnesium ion concentration is only constrained by the limits of solubility of magnesium in aqueous solution and a desire to have the endodeoxyribonuclease present in the same composition in an active conformation.

Also contemplated by the present invention are compositions containing an endodeoxyribonuclease enzyme of the present invention, single-stranded DNA, magnesium ion at a concentration of greater than 20 millimolar and a polyamine.

Preferably, the polyamine is spermidine, putrescine, or spermine. More preferably, the polyamine is spermidine and is present at a concentration of about 2 mM to about 10 mM.

Also contemplated by the present invention are composition containing an endodeoxyribonuclease enzyme of the present invention, single-stranded DNA, magnesium ion at a concentration of greater than 20 millimolar, a second single-stranded DNA molecule ending in a 3'-terminal hydroxyl, and a third single-stranded DNA molecule having a guanine nucleotide at its 5'-terminal end.

Also contemplated by the present invention are compositions containing an endodeoxyribonuclease enzyme of the present invention, singled-stranded DNA and magnesium ion at a concentration of greater than 20 millimolar, wherein said single-stranded DNA is greater in length than the recognition site present on the endodeoxyribonuclease enzyme.

EXAMPLES

The following examples illustrate, but do not limit, the present invention.

1. Preparation of Endodeoxyribonucleases.

The wild-type and mutant ribozymes were produced by first isolating the 443 base-pair Eco RI to Hind III restriction endonuclease fragment from the plasmid PT7-21 described by Zaug et al., *Biochemistry,* 27:8924 (1988) using the standard methods described in *Current Protocols in Molecular Biology,* Ausubel et al., eds. John Wiley and Sons, New York (1987).

This 443 base-pair fragment contains the T7 promoter described by Dunn et al., *J. Mol. Biol.,* 166:477–535 (1983) and residues 22–414 of the Tetrahymena IVS and residues 1–25 of the 3' Tetrahymena exon described by Been et al., *Cell,* 47:207–216 (1986). This Eco RI and Hind III fragment was inserted into the M13 vector, M13mp18 that is similar to the vector described by Yanisch-Perron et al., *Gene,* 33:103–119 (1985), that had been previously cleaved with Eco RI Hind III, and using standard subcloning procedures described in *Current Protocols in Molecular Biology,* Ausubel et al, eds. John Wiley and Sons, New York (1987). The resulting M13T7L-21 DNA construct was transformed into *E. coli* host cells according to the transformation procedure described in *Molecular Cloning: A Laboratory Manual,* Maniatis et al., eds., Cold Spring Harbor Laboratories, Cold Spring Harbor, N.Y. (1989). Single stranded DNA was then prepared from the M13T7L-21 transformed cells according to the procedures described in *Current Protocols in Molecular Biology,* Ausubel et al, eds. John Wiley and Sons, New York (1987). The accuracy of the above construction was confirmed by DNA sequencing using the klenow fragment of *E. coli* DNA polymerase I (Boehringer Mannheim Biochemicals, Indianapolis, Ind.) and the dideoxynucleotide sequencing method described by Sanger et al., *Proc. Natl. Acad. Sci., USA,* 74:5463–5467 (1977).

The wild-type and mutant ribozymes were prepared directly from the single-stranded M13T7L-21 DNA using a modification of the technique previously described by Joyce and Inoue, *Nucleic Acid Research,* 17:711–722 (1989). The technique involves construction of a template strand that optionally includes one or more mutagenic oligodeoxynucleotides. The resulting partially-mismatched double-stranded DNA is transcribed directly using T7 RNA polymerase. Briefly, a five fold molar excess of a terminator polynucleotide and a mutator oligo were admixed with 5 µg of single-stranded M13T7L-21 DNA and a solution containing 20 mM tris[hydroxy-methyl]aminomethane adjusted to pH 7.5 with HCl(Tris-HCl), 50 mM NaCl and 2 mM $MgCl_2$. This solution was maintained at 70 degrees centigrade (70° C.) for 5 minutes and then steadily cooled to 30° C. over 40 minutes. Fifteen units(U) of T4 DNA ligase (U.S. Biochemicals, Cleveland, Ohio) and 7.5 U of T4 DNA polymerase (U.S. Biochemicals) were admixed to the solution together with sufficient amounts of reagents to make the solution contain a final concentration of 20 mM Tris-HCl at pH 7.5, 50 mM NaCl, 5 mM $MgCl_2$, 2 mM dithiothreitol (DTT), 1 mM adenosine triphosphate (ATP) and 0.5 mM each of dGTP, dTTP, dATP and dCTP (dNTPs). The resulting solution was maintained at 37° C. for 60 minutes to complete the synthesis of the mutant strand. The resulting DNA was purified by ethanol precipitation and then used to direct the transcription of mutant RNA.

Transcription took place either in a 10 µl volume containing 1 µg of mutant DNA, 2 µCi [$\alpha^{32}P$] GTP and 50 U of T7 RNA polymerase that was prepared as previously described by Davanloo et al., *Proc. Natl. Acad. Sci., USA*, 81:2035–2039 (1984), and purified according to a procedure originally developed by Butler & Chamberlain, *J. Bio. Chem.*, 257:5772–5779 (1982), or in a 400 μl volume containing 10 μg of mutant DNA, 40 μCi [$^3$H]UTP and 2,400 U of T7 RNA polymerase. In either case, the transcription mixture also contained 40 mM Tris-HCl at pH 7.5, 15 mM MgCl$_2$, 10 mM dithiothreitol, 2 mM spermidine, and 1 mM (each) NTPs, and was incubated at 37° C. for 90 minutes. The T7 RNA polymerase was extracted with phenol and the transcription products were purified by ethanol precipitation. The mutant RNA was isolated by electrophoresis in a 5% polyacrylamide/8 M urea gel, eluted from the gel, and purified by ethanol precipitation and chromatography on Sephadex G-50.

The Delta P2 mutant was prepared using the mutagenic oligodeoxynucleotide 01 (Table 1 and FIG. 3). The partially-randomized Delta P2 mutant was prepared using the mutagenic oligodeoxynucleotide 02 (Table 1 and FIG. 3). The Delta P5 mutant was prepared using mutagenic oligonucleotides 03 or 04 (Table 1 and FIG. 3). The Delta P6 mutant was prepared using the mutagenic oligodeoxynucleotide 05 (Table 1 and FIG. 3). The Delta P6b mutant was prepared using the mutagenic oligodeoxy-nucleotide 06 (Table 1 and FIG. 3). The Delta P9 mutant was prepared using the mutagenic oligodeoxy-nucleotide 07 (Table 1 and FIG. 3).

Wild-type and mutant RNAs other than those containing the Delta P9 deletion were defined at their 3' end by the oligodeoxynucleotide 08 (Table 1 and FIG. 3). Mutants containing the Delta P9 deletion were defined by the Delta P9 mutagenic oligo which directs a transcript that includes 10 nucleotides of the 3' exon.

TABLE 1

| | |
|---|---|
| 01) | 5'-TTTGACGGTCTTGTTCCCTCCTATAGTGAG-3' |
| 02) | 5'-TTTGACGGTCTNNNNCCCTCCTATAGTGAG-3' |
| 03) | 5'-TGCGTGGTTACTTTCCCGCAA-3' |
| 04) | 5'-GGACTTGGCTGCGTGGTTACTTTCCCGCAA-3' |
| 05) | 5'-TTTAGTCTGTGAACTCTTGGC-3 |
| 06) | 5'-TCTGTGAACTGCATCCAAGCTTAGGACTTGG-3' |
| 07) | 5'-GGCTACCTTACGAGTACTCCGACTATATCTTAT-3' |
| 08) | 5'-CGAGTACTCCAAAAC-3' |

The 3' exon sequence was removed by RNA-catalyzed site-specific hydrolysis as has been previously, Inoue et al., *J. Mol. Biol.*, 189:143–165 (1986). Briefly, the RNA was incubated in the presence of 50 mM CHES at pH 9.0 and 10 mM MgCl$_2$ at 42° C. for 1 hour. Wild-type and mutant RNAs were isolated by electrophoresis in a 5% polyacrylamide/8M urea gel, eluted from the gel, and purified by affinity chromatography on du Pont Nensorb (du Pont Company, Wilmington, DE). RNAs were sequenced by primer extension analysis using AMV reverse transcriptase (Life Technologies, Inc., Gaithersburg, Md.) in the presence of dideoxynucleotides, using a modification of the methods described by Sanger et al., *Proc. Natl. Acad. Sci., USA*, 74:5463–5467 (1977), except for those containing the Delta P9 deletion, which were sequenced from the 3' end by partial RNase digestion, Donis-Keller et al., *Nucleic Acids Res.*, 15:8783–8798 (1987).

The RNA substrate 5'-GGCCCUCUA$_{13}$-3' was prepared by in vitro transcription using a partially single-stranded synthetic DNA template according to the methods described by Milligan et al., *Nucleic Acids Res.*, 4:2527–2538 (1977). The template contains both strands of the promoter for T7 RNA polymerase (positions −17 through +1) followed by the single-stranded template sequence 3'-CGGGAG-AT$_{10}$-5'. Run-off transcripts of the form 5'-GGCCCUCUA$_n$-3', where n=9–16, were obtained. The resulting products were separated by electrophoresis in a 20% polyacrylamide/8M urea gel, eluted from the gel, purified by affinity chromatography on du Pont Nensorb, and sequenced by partial RNase digestion Donis-Keller et al., *Nucleic Acids Research*, 15:8783–8798 (1987). RNA substrates having the sequence 5'-GGCCCUCUA$_{13}$-3' were used throughout this study.

The DNA substrates were either purchased from a number of commercial sources (i.e., Research Genetics, Huntsville, Ala.) or synthesized using an Applied Biosystems (Foster City, Calif.) oligonucleotide synthesizer according to the manufacture's instructions.

2. Cleavage of single-stranded DNA by Endodeoxyribonuclease

The ability of the Delta P9 mutant and wild-type ribozymes to cleave three different substrates was determined. The reactions were carried out by admixing 0.02M of the ribozyme, 2.0 μM of either GGCCCUCU.A$_3$UA$_3$UA$_3$ (S1) or d(GGCCCTCU.A$_3$TA$_3$TA) (S2) or d(GGCCCTCT.A$_3$TA$_3$TA) (S3), 30 mM N-[2-hydroxyethyl]-piperazine-N'-[3-propane-sulfonic acid] (EPPs) at pH 7.5, 50 mM MgCl$_2$ and 2 mM spermidine. The resulting solution was maintained at 50° C. for one hour. The resulting reaction products were separated by electrophoresis in a 5% polyacrylamide/8 m urea gel. The gel was used to expose x-ray film to produce an autoradiogram shown in FIG. 4.

The Delta P9 ribozyme cleaves the RNA substrate, S1 the modified DNA substrate, S2, and the DNA substrate S3 (FIG. 4).

3. Selection of Mutant Ribozymes Capable of Cleaving DNA.

Mutant Ribozymes capable of cleaving a DNA substrate were selected using the in vitro evolution system described by G. F. Joyce, *Gene*, 82:83–87 (1989). This technique allows a structural variant of Tetrahymena ribozyme capable of catalyzing a specific reaction to be selectively amplified from a population of Tetrahymena ribozyme structural variants.

This in vitro evolution technique was used to select a Tetrahymena ribozyme structural variant that cleaves a polydeoxyribonucleic acid (FIG. 5). The first step in this technique is the ribozyme trans-splicing reaction involving the attack by its 3'-terminal guanosine at a phosphodiester bond following a sequence of pyrimidines located within a RNA substrate previously described by G. F. Joyce, *Gene*, 82:83–87 (1989). The product of the reaction is the ribozyme joined to the substrate sequence that lies downstream from the target phosphodiester (FIG. 5, top). Selection occurs when an oligodeoxynucleotide primer is hybridized across the ligation junction and used to initiate synthesis of complementary using reverse transcriptase DNA (FIG. 5, bottom). The primer ligation junction does not bind to unreacted starting materials (<10$^{-6}$ compared to reaction products, at or below the limits of detection), and thus leads to selective reverse transcription of reactive materials. In order to amplify the selected materials, a primer containing one strand of a promoter for T7 RNA polymerase is hybridized to the extreme 3' end of the cDNA, the second strand of the promoter is completed using a DNA-dependent DNA polymerase, and the DNA is transcribed to RNA as has been previously described by Joyce, G. F. in *Molecular Biology of RNA, UCLA Symposia on Molecular and Cellular Biology*, ed., Cech, T. R., 94:361–371, Alan R. Liss, New York, (1989) and Kwoh et al., *Proc. Natl. Acad. Sci., USA*, 86, 1173–1177 (1989).

The selected material is amplified at the transcription level due to the high turnover of T7 RNA polymerase that has been previously described by Chamberlin et al., in *The Enzymes*, ed. P. Boyer, pp. 87–108, Academic Press, New York (1982). Mutations can be introduced by replacing a portion of the cDNA with one or more mutagenic oligodeoxynucleotides and transcribing the partially-mismatched template directly as has been previously described by Joyce et al., *Nucleic Acid Research*, 17:711–722 (1989). Ribozymes produced in this way can also be internally labelled with $^{32}$P-GTP.

The ability of a population of wild-type and mutant forms of the Tetrahymena ribozyme to cleave the RNA substrate GGCCCUCUAAAUAAAUA (S1), the modified DNA substrate d(GGCCCTCUAAATAAATA) (S2), and the DNA substrate d(GGCCCTCTAAATAAATA) (S3) was determined. Briefly, 1 μM each of internally labelled wild-type, Delta P6, Delta P2, Delta P9, Delta P6/P9 and Delta P2/P9 ribozymes were admixed with 2 μM of either the S3 DNA substrate or the S1 RNA substrate, 30 mM EPPS at pH 7.5, 50 mM MgCl$_2$ and 2 mM spermidine were admixed to form endodeoxyribonuclease reaction admixtures. The endodeoxyribonuclease reaction admixture was maintained at 50° C. for one hour. The cleavage of substrate by each of these ribozymes is detected as the appearance of a slower migrating ribozyme caused by the ligation of the cleaved substrate to the ribozyme (FIG. 6, Lanes 2 and 3).

Focusing on the DNA substrate S3, two rounds of selective amplification were performed to recover the nucleic acid enzymes, in this case endodeoxyribonucleases, capable of cleaving DNA from a collection of ribozyme structural variants including, wild-type, Delta P6, Delta P2, Delta P9, Delta P6/P6, and Delta P2/P9. These structural variants (1 μM, internally labelled with 1 μCi/nmole $^{32}$P-GTP) were admixed with 2 μM DNA substrate S3, 30 mM EPPS at pH 7.5, 50 mM MgCl$_2$ and 2 mM spermidine and maintained at 50° C. for 1 hour. The first round of cDNA synthesis was carried out by admixing a 20-fold excess of d(TAT$_3$AT$_3$CGAGT) primer, heating the solution to 65° C. for 5 minutes in the presence of 50 mM Tris-HCl at pH 7.5 and 5 mM DTT and then rapidly cooling the solution to 0° C. The solution was then made to contain 6 mM MgCl$_2$, 100 μM (each) dNTPs and 1 U/μl of AMV reverse transcriptase. The resulting solution was maintained at 37° C. for 20 minutes. A small aliquot of the solution was removed and analyzed by electrophoresis in a 5% polyacrylamide /8M urea gel. After the first cDNA synthesis, the selected reverse transcriptant of the Delta P6, Delta P2, Delta P9, and Delta P2/9 ribozymes can be seen in Lane 5 of FIG. 6.

The RNA is destroyed by alkaline hydrolysis and the monomers removed by ethanol precipitation. RNA was transcribed from the cDNA by admixing a 20-fold excess of d(ATCGATAATA CGACTCACTATAGGAGGGAAAAGTTATCAGGC) primer, heating the resulting solution to 65° C. for 5 minutes in the presence of 50 mM Tris-HCl at pH 7.5 and 5 mM DTT and then rapidly cooling the solution to 0° C. The solution is then made to contain 15 mM MgCl$_2$, 2 mM spermidine, 100 μM (each) dNTPs, 2 mM (each) NTPs 1 U/μL AMV reverse transcriptase, 0.2 U/μL DNA polymerase I (Klenow fragment) and 20 U/μL of T7 RNA polymerase. The solution was maintained at 37° C. for 1 hour to allow RNA to be transcribed from the cDNA. This step results in a large amplification of the ribozymes having the desired catalytic activity (FIG. 6, Lane 6, 1/50 of the material).

A second round of cDNA synthesis was performed using an equal molar mixture of the primers d(CGAGTACTCCAAAC) and d(CGAGTACTCCGAC) to restore the 3' end of the RNA. The remainder of the cDNA synthesis was performed as above. The resulting reaction products were analyzed by electrophoresis (FIG. 6, Lane 7).

A second round of RNA synthesis was performed using the remaining reaction mixture using the RNA synthesis conditions described above. A portion representing 1/50 of the resulting reaction products were analyzed by gel electrophoresis and are shown in FIG. 6, Lane 8.

This system allowed the selection of a ribozyme having a desired catalytic activity from a mixture of ribozymes.

The foregoing specification, including the specific embodiments and examples, is intended to be illustrative of the present invention and is not to be taken as limiting. Numerous other variations and modifications can be effected without departing from the true spirit and scope of the present invention.

I claim:

1. A method for specifically cleaving a single-stranded DNA molecule, comprising the steps of:
   (a) providing a first RNA molecule that is a group I intron that cleaves a second RNA molecule to leave a 3'-OH, said first RNA molecule having a deoxyribonuclease activity; and
   (b) contacting said first RNA molecule with said single-stranded DNA molecule under conditions which allow said first RNA molecule to cause said single-stranded DNA molecule to be cleaved, said conditions including providing Mg$^{2+}$ ions and guanosine or guanosine triphosphate at a pH between about 6.0 and about 9.0 and a temperature between about 15° C. and about 60° C.

2. The method of claim 1, further comprising providing said RNA molecule in a reaction medium at a concentration sufficient to cause cleavage of at least 1% of a population of the DNA molecules in an hour.

3. The method of claim 1, further comprising providing said RNA molecule in a reaction medium at a concentration sufficient to cause cleavage of at least 10% of a population of the DNA molecules in an hour.

4. The method of claim 1, wherein said RNA molecule comprises the portions of an RNA molecule of Tetrahymena having said deoxyribonuclease activity.

5. The method of claim 1, wherein said RNA molecule comprises a binding site for single-stranded DNA, which binding site is complementary to nucleotides adjacent to a cleavage site on said single-stranded DNA molecule.

* * * * *